United States Patent [19]

Huang

[11] Patent Number: 4,889,868

[45] Date of Patent: * Dec. 26, 1989

[54] BIS-IMIDAZOLINOAMINO DERIVATIVES AS ANTIALLERGY COMPOUNDS

[75] Inventor: Fu-chih Huang, Leonia, N.J.

[73] Assignee: Rorer Pharmaceutical Corporation, Fort Washington, Pa.

[*] Notice: The portion of the term of this patent subsequent to May 13, 2003 has been disclaimed.

[21] Appl. No.: 809,649

[22] Filed: Dec. 16, 1985

Related U.S. Application Data

[63] Continuation-in-part of Ser. No. 684,214, Dec. 20, 1984, Pat. No. 4,588,737.

[51] Int. Cl.$^4$ .................. A61K 31/415; C07D 405/12; C07D 405/14

[52] U.S. Cl. .................................... 514/392; 514/401; 514/402; 548/315; 548/316; 548/348; 548/350; 548/351

[58] Field of Search ............... 548/300, 315, 316, 336, 548/337, 339, 341, 342, 343, 347, 348, 350, 351, 352; 514/392, 401, 402

[56] References Cited

U.S. PATENT DOCUMENTS 4,588,737  5/1986  Huang .................................. 514/392

*Primary Examiner*—Richard A. Schwartz
*Attorney, Agent, or Firm*—Gilbert W. Rudman; Imre (Jim) Balogh

[57] ABSTRACT

This invention relates to chemical compounds which possess valuable therapeutic activity particularly as lipoxygenase and phospholipase C inhibitors and as platelet-activating factor receptor antagonists. The compounds posses anti-inflammatory anti-asthmatic and anti-allergic properties and are additionally useful for the treatment of myocardial infarctions. The compounds of this invention are imidazolino-containing compounds of the general formula:

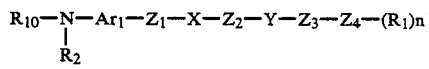

47 Claims, No Drawings

BIS-IMIDAZOLINOAMINO DERIVATIVES AS ANTIALLERGY COMPOUNDS

This application is a continuation in Part of U.S. application Ser. No. 684,224, which was filed on Dec. 20, 1984, now U.S. Pat. No. 4,588,737.

This invention relates to new chemical compounds which posses valuable therapeutic activity particularly as lipoxygenase and phospholipase C inhibitors and platelet-activating factor receptor antagonists. These compounds possess anti-inflammatory, anti-asthmatic and antiallergic properties and are additionally useful for the treatment of myocardial infarctions.

U.S. Pat. Nos. 4,327,102 and 4,394,509 describe sulfoxides of the formula:

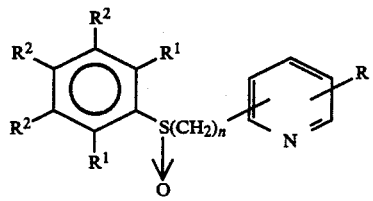

in which R is hydrogen or a hydrocarbon radical, $R^1$ is H or F, $R^2$ is H, F, Cl or $CF_3$, and n is 1 or 2, as anti-ulcer and/or anti-secretory compounds, as well as the corresponding thioether compounds, which are prepared by oxidation of the thioether sulfur to the sulfone. The thioethers of the said structure are also described in U.S. Pat. Nos. 4,415,579; 4,394,509 and 4,337,259 as anti-ulcer compounds.

I. Eur. J. Med. Chem. -Chem. Ther.-198318 (pp. 277–285), described compounds of the following structures as anti-secretory agents:

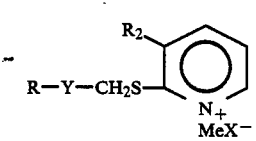
A.

R = various heterocyclics, cyclohexyl, various substituted phenyls;
Y = $CH_2$, S, $(CH_2)_2$, $(CH_2)_3$, CHMe, C=O, C=C;
$R_2$ = H, CHO, $CH(OEt)_2$

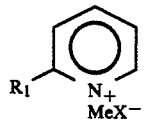
B.

$R_1$ is benzyloxypyridyl quaternary salts, phenylthiomethyl, benzylsulfoxy, benzylthio, etc.

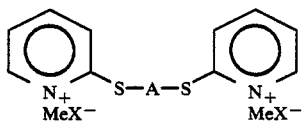
C.

A = alkylene up to $C_5$, and

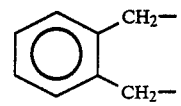

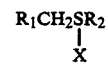
D.

$R_1$ and $R_2$ = various heterocycles, phenyl, substituted phenyl
X = —, O, or $O_2$.

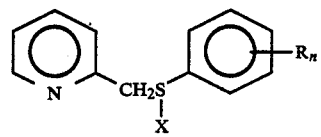
E.

$R_n$ = H, halogen, or methoxy.

The present new compounds are of the formula:

$$R_{10}-\underset{R_2}{N}-Ar_1-Z_1-X-Z_2-Y-Z_3-Z_4\,(R_1)_n \qquad I$$

or pharmaceutically acceptable salts thereof; wherein
$Ar_1$ is independently phenyl, naphthyl, or a nitrogen, oxygen or sulfur heterocyclic ring;
X and Y are independently O, S or a chemical bond;
$Z_1$ and $Z_3$ are each a chemical bond or alkylene chain containing up to 8 carbon atoms in the principal chain and up to a total of 12 carbon atoms;
$Z_2$ and $Z_4$ are each a chemical bond, alkylene chain containing up to 6 carbon atoms in the principal chain and a total of up to 10 carbon atoms, aryl, cycloalkyl, or a nitrogen, oxygen, sulfur heterocyclic ring;
each $R_1$ is independently hydrogen, lower alkyl, aryl, lower aralkyl, hydroxy, lower alkoxy, carboxy, lower carbalkoxy, lower carbaralkoxy, lower carbaryloxy, loweralkoxy carbonyl, lower alkanoyl, cyano, halogen, amino, loweralkyl amino, diloweralkylamino, thiol, loweralkylmercapto, lower alkenyl, lower alkynyl, lowercycloaklyl,

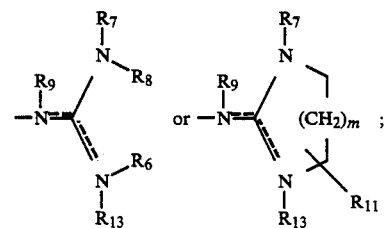

$R_2$, $R_5$, $R_7$, $R_9$ and $R_{13}$ are independently hydrogen, lower alkyl or lower alkanoyl; but when the nitrogen to which $R_2$ is attached contains a double bond, $R_2$ is —, when the nitrogen to which $R_9$ is attached contains a double bond, then $R_9$ is —, or when the nitrogen to which $R_{13}$ is attached contains a double bond, then $R_{13}$ is —;
$R_3$, $R_4$, $R_6$ and $R_8$ are independently hydrogen, lower alkyl, cyano, or nitro;

$R_{10}$ is

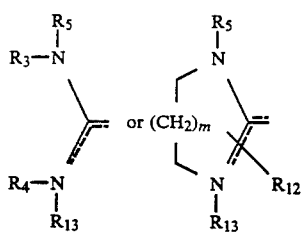

$R_{11}$ and $R_{12}$ are independently hydrogen, or lower alkyl;

n is 0, 1, 2, or 3 and m is 0, 1, or 2;

provided that when $Z_2$ is a chemical bond or methylene group, X and Y cannot be both oxygen or sulfur simultaneously.

The heterocyclic groups exemplary of $Ar_1$, $Z_2$ and $Z_4$ are 5-10 membered rings containing at least one oxygen, sulfur or nitrogen. These heterocyclic compounds may be unsaturated, partially saturated or aromatic and also include the so-called benzoheterocyclic rings. Exemplary heterocyclics include furan, thiophene, pyrrole, piperidine, dihydrofuran, tetrahydrofuran, dihydrothiophene, pyridine, thiazole, piperazine, oxazole, benzofuran, tetrahydroquinoline, quinoline, indole, dihydroindole, benzothiophene, dihydrobenzothiophene, benzoxazole and similar heterocyclic rings. The preferred heterocyclic ring is tetrahydrofuran.

The non-heterocyclic aryl moieties of $Z_2$ and $Z_4$ include phenyl, α- or β-naphthyl, etc. The preferred non-heterocyclic aryl moiety is phenyl. $Ar_1$ is preferably phenyl.

The non-heterocyclic aryl and the heterocyclic groups representative of $Ar_1$, $Z_2$, and $Z_4$ may be mono- or di-substituted with such groups as hydrogen, halogen, hydroxy, lower alkyl, lower alkoxy, amino, lower alkyl amino, di(lower) alkylamio, mercapto, loweralkythio, nitro, trifluoromethyl, aryl, aryloxy, lower aralkyl, lower aralkoxy, carboxy, loweralkylcarboxy, arylcarboxy, lower carbalkoxy, carboxamide, lower alkanoyl, formyl, sulfonyl, benzyloxy, aryloxy, phenoxy, and the like.

The cycloalkyl groups may be mono-, bi- or polycyclic and contain from 3 to 20 carbons. These groups include cyclopropyl, cyclopentyl, cyclohexyl, cycloheptyl, bornyl, norbornyl, indanyl and the like. These groups may be partially unsaturated and carry substituents such as hydrogen, halogen, hydroxy, lower alkyl, lower alkoxy, lower aralkoxy, amino, lower alkylamino, di (loweralkyl) amino, thiol, lower alkylmercapto, nitro, trifluoromethyl, aryl, aryloxy, and the like.

Exemplary alkanoyl groups include acetyl, propionyl, butyryl, valeryl, isobutyryl, pivaloyl, neopentyl carbonyl, octanoyl, and decanoyl.

The alkyl groups, either alone or within the various substituents defined hereinbefore are preferably lower alkyl which may be straight or branched chain and include methyl, ethyl, propyl, isopropyl, butyl, isobutyl, amyl, hexyl and the like.

The halo atoms in halo an trihalomethyl are Cl, Br, I and F.

The alkenyl and alkynyl groups represented of $R_1$ may be normal or branched chains. These groups contain preferably 2 to 6 carbon atoms and may contain up to 2 double or triple bonds. But, multiple bonds may not be attached directly to aryl moieties, wherever present, in $Z_4$ or $Z_2$.

The alkylene chain representative of $Z_1$, $Z_2$, $Z_3$ and $Z_4$ can be branched or straight chain containing up to 6 carbon atoms in the principal chain and up to a total of 10 carbon atoms. It is preferred that $Z_1$, $Z_2$, $Z_3$ are independently a chemical bond or alkylene chain containing up to 3 carbon atoms in the principal chain. Whenever $Z_1$, $Z_2$, $Z_3$ or $Z_4$ is an alkylene chain, it may carry substituents such as hydrogen, lower alkyl, aryl, lower alkyl, hydroxy, lower alkoxy, lower aralkoxy, aryloxy, carboxy, halogen, amino, lower alkylamino, di(lower) alkylamino, mercapto, lower alkylthio, carboxy, lower carbalkoxy, carbaryloxy, lower alkanoyl, formyl and the like. Whenever $Z_1$, $Z_2$, $Z_3$, $Z_4$ are independently other than a chemical bond, it is preferred that $Z_1$, $Z_2$, $Z_3$ and $Z_4$ are monosubstituted with hydrogen, lower alkyl, aryl, lower aralkyl, hydroxy, lower alkoxy, lower aralkoxy or aryloxy.

It is preferred that X and Y are each independently oxygen or a chemical bond. The preferred $R_2$ group is hydrogen. In addition, it is preferred that $R_{10}$ is

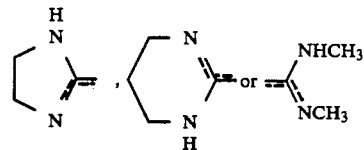

Moreover, it is preferred that $R_1$ is H, lower alkoxy,

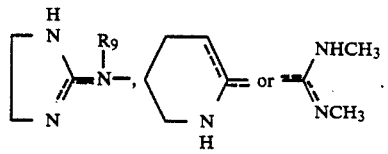

Preferred compounds are of the formula

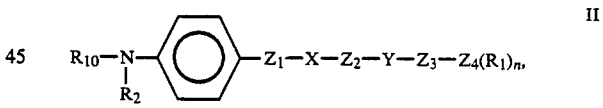

wherein $R_1$, $R_2$, $R_{10}$, $Z_1$, $Z_2$, $Z_3$, $Z_4$, X and Y, and n have the aforementioned meanings.

Further preference exists for compounds having the following formulas:

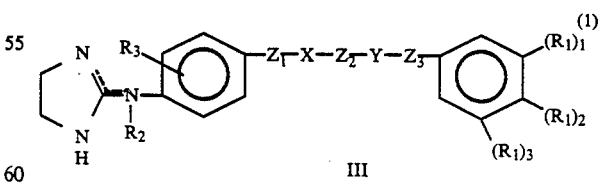

wherein:

X is a chemical bond or oxygen;

Y is a chemical bond or oxygen;

$Z_1$ and $Z_3$ are independently a chemical bond or an unsubstituted normal alkylene chain of up to 5 carbon atoms;

$Z_2$ is a chemical bond,

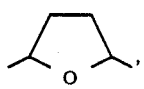

or an unsubstituted normal alkylene chain of up to 5 carbon atoms or a substituted alkylene chain having up to 5 carbon atoms in the principal chain wherein the substitution is methoxy or ethoxy;

$(R_1)_1$ is hydrogen, methoxy, methyl or chloro;

$(R_1)_2$ is hydrogen, methoxy, or

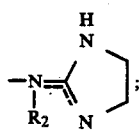

$(R_1)_3$ is hydrogen or methoxy;

$R_3$ is hydrogen, methyl or chloro; and $R_2$ is hydrogen or acetyl; but when the nitrogen to which $R_2$ is attached contains a double bond, then $R_2$ is —.

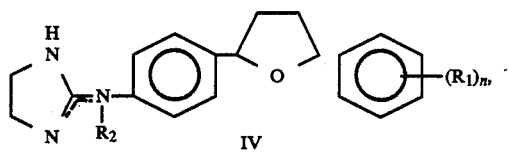

(2)

wherein $R_1$ is hydrogen, lower alkoxy,

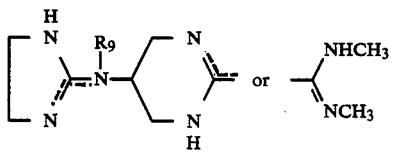

$R_2$ is hydrogen but when the nitrogen to which $R_2$ is attached contains a double bond, then $R_2$ is —,

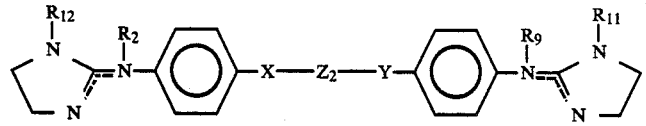

wherein $Z_2$ is an alkylene chain of up to 8 carbon atoms in the principal chain and up to a total of 12 carbon atoms which may be mono- or di-substituted with hydrogen, lower alkyl, phenyl, benzyl or lower alkoxy, X and Y are independently oxygen, sulfur or a chemical bond; and $R_2$, $R_9$, $R_{11}$ and $R_{12}$ are independently hydrogen, lower alkyl or lower alkanoyl, but when the nitrogen to which $R_2$ is attached contains a double bond, then $R_2$ is —, or when the nitrogen to which $R_9$ is attached contains a double bond, then $R_9$ is —.

Especially preferred compounds of Formula V are those in which the alkylene chain represented by $Z_2$ contains from 4 to 6 carbon atoms in the principal chain.

Of the substituents on $Z_2$, the preferred are lower alkyl, e.g., methyl, ethyl, and isopropyl. Further preference exists for compounds in which X and Y are oxygen and $R_{12}$, $R_2$ $R_9$, and $R_{11}$ are each hydrogen.

The compounds of the present invention may contain one or more asymmetric carbon atoms and may exist in racemic and optically active forms. All of these compounds are contemplated to be within the scope of the present invention.

The present compounds can be prepared by art-recognized procedures from known compounds or readily preparable intermediates.

The following general procedure can be employed.

For example, an amine of Formula VI is reacted with an amidine or imidazole of Formula VII as follows:

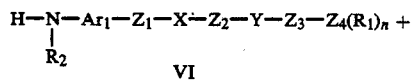

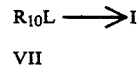

wherein the substitutients are as previously described and L is a leaving group known in the art, such as $SCH_3$, Cl, Br, etc.

Furthermore, in those instances wherein $Z_4$ is phenyl, $R_1$ is

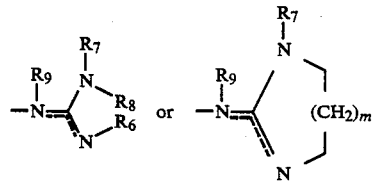

and $R_9$ has the same meaning as $R_2$ then the following general procedure can also be employed:

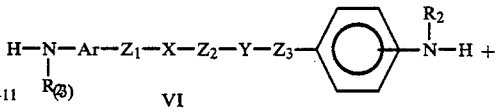

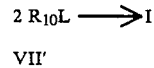

The substituents are as previously defined.

The synthetic procedure is predicated on the removal of the reactive hydrogen on position-2 of the imidazoline or amidino reactant and the formation of a bond with each of the amino groups on $Ar_1$ and the phenyl ring of $Z_4$. This condensation can be effected in the presence of a variety of compounds known for this purpose, e.g., phosphorus oxychloride, thionyl chloride and like compounds. In a preferred mode, it is advantageous to block the secondary amino nitrogen of the amidine or imidazoline ring to avoid secondary or competing reactions, particularly when phosphorus oxychloride or thionyl chloride is used. Any blocking group can be employed for this purpose, the preferred being groups which are readily hydrolyzable such as lower alkanoyl groups, e.g., acetyl, propionyl, butynyl and the like. Of course, where R in the amidine or imidazoline moiety is to be other than H, e.g., alkyl, alkanoyl, etc., no blocking group is required.

A further preparative procedure involves the use of an imidazoline substituted in the 2-position with a leaving group which combines with a hydrogen of the amino nitrogen of the formula VII compound. Such leaving groups are well known in the art and preference resides in the use of such leaving groups which combine with the aforesaid hydrogen to form compounds which are substantially unreactive with the reactants and products under the preparative experimental conditions.

The aforesaid reactions can be carried out at room temperature or at elevated temperatures up to the reflux temperature of the reaction mixture. The use of temperatures higher than room temperature usually will merely shorten the reaction time which can be determined by monitoring the mixture periodically using known techniques, e.g., chromatographic techniques. Usually the reactions are effected in a solvent for efficiency of reaction as is commonly appreciated by those in the art. Solvents are not always required, since liquid reactants, e.g., $POCl_3$ or $SO_2Cl_2$, can serve as solvents as well.

An alternative procedure for preparing the bisimidazoline structure VIII, a subgeneric class of compounds of Formula I,

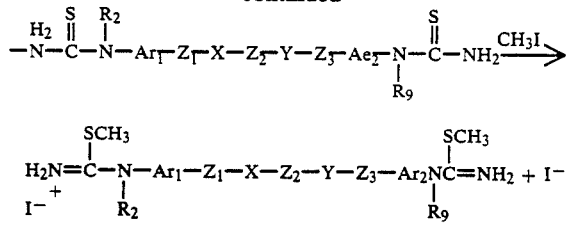

is via the reaction of 1,2-ethyl diamine with the bis amidine of formula IX:

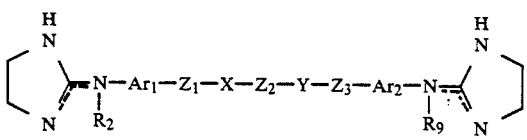

or salts thereof; wherein $R_2$, $Ar_1$, $Z_1$, $X$, $Z_2$, $Z_3$, $Ar_2$, $R_9$, are as defined heretofore and L and $L_1$ are good leaving groups such as $SCH_3$.

Compounds of the Formula IX can be prepared by synthetic techniques known in the art. An exemplary sequence is as follows:

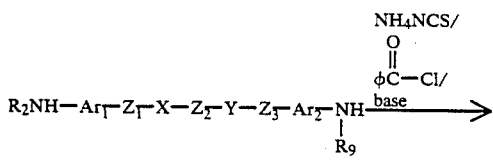

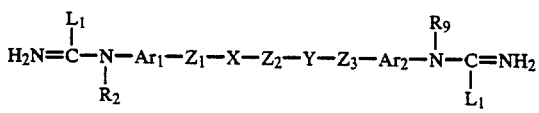

The products are obtained by classical methods or recovery from the reaction mixture.

It is possible to effect further reactions on the formed products such as introduction of alkyl or alkanoyl groups on available positions of the amino nitrogens in the product using known methods such as alkylating or acylating reactions.

The starting compounds for production of the present new compounds are either known or readily preparable as illustrated in the examples which are included herein.

Various substituents on the present new compounds, e.g., as defined in $Ar_1$, $Z_1$, $Z_2$, $Z_3$, and $Z_4$ can be present in the starting compounds, can be added to any one of the intermediates or added after formation of the final products by the known methods of substitution or conversion reactions. If the substituents themselves are reactive, then the substituents can themselves be protected according to the techniques known in the art. A variety of protecting groups known in the art may be employed. Examples of many of these possible groups may be found in "Protective Groups in Organic Synthesis" by T. W. Green, John Wiley and Sons, 1981. For example, the nitro groups can be added to an aromatic ring by nitration and the nitro group converted to other groups, such as amino by reduction, and halo by diazotization of the amino group and replacement of the diazo group. Alkanoyl groups can be substituted onto the aryl groups by Friedel-Crafts acylation. The acyl groups can then be transformed to the corresponding alkyl groups by various methods, including the Wolff-Kishner reduction and Clemmenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product. The present new compounds contain basic nitrogen and can form salts with acids. All such acid salts are contemplated by the invention but especially preferred are salts with pharmaceutically acceptable acids, such as hydrochloric, sulfuric, nitric, toluenesulfonic, acetic, propionic, tartaric, malic and similar such acids well known in this art. In addition, quaternary salts can be formed using standard techniques of alkylation employing, for example, hydrocarbyl halides or sulfates such as methyl, ethyl, benzyl, propyl or allyl halides or sulfates.

The compounds of the present invention can be administered to the host in a variety of forms adapted to the chosen route of administration, i.e., orally, intravenously, intramuscularly or subcutaneous routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate, a disintergrating agent such as corn starch, alginic acid and the like; a lubricant such as magnesium stearate; and a sweetening agent such as sucrose, lactose or saccarin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propyl parabens as preservatives, a dye and flavoring such as cherry or orange flavor. Of course, any material used in preparing any dosage unit form should be pharmaceutically pure and substantially non-toxic in the amounts employed. In addition, the active compounds may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions of dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The following examples further illustrate the invention.

EXAMPLE 1

1,6-Bis(p-nitrophenyl)-1,5-hexadiene

To a solution of 0.76 g of sodium in 50 ml of absolute EtOH was added 12.25 g of butane-1,4-bis-triphenyl phosphonium bromide. Ten minutes later, 5 g of p-nitrobenzaldehyde was then added. The reaction mixture was stirred at room temperature overnight and the solvent was removed in vacuo. The residue was treated with $CH_2Cl_2$. The organic solution was washed with $H_2O$, dried with ($MgSO_4$), and concentrated to give 0.5 g of product as a yellow solid.

EXAMPLE 2

1,6-Bis-(p-aminophenyl)hexane

A mixture of 0.49 g of the Example 1 product and 0.2 g of 5% Pd/C in 50 ml of EtOH was hydrogenated at 45 psi for 3 hours. After filtration (Celite), the filtrate was concentrated to give 0.2 g of product as a white solid.

EXAMPLE 3

1,6-Bis[N-[2-(1-acetyl)imidazolino]-4-aminophenyl]hexane

A solution of 0.2 g of the Example 2 product and 0.19 g of N-acetyl 2-imidazolone in 10 ml of $POCl_3$ was heated at 50° C. for 2 days. Most $POCl_3$ was removed in vacuo and the residue was treated with $H_2O$. The aqueous solution was basified and extracted with $CH_2Cl_2$. The organic solution was separated, dried and concentrated. The crude product, after column chromatography purification gave 0.2 g of product as a white solid.

EXAMPLE 4

1,6-Bis[N-(2-imidazolino)-4-aminophenyl]hexane

A solution of 0.3 g of the Example 3 product in 20 ml of 25% NaOH and 10 ml dioxane was heated at 60° C. overnight. The aqueous solution was acidified to pH 2 and was extracted with ether. The aqueous solution was then rebasified with 1N NaOH to pH 8. The precipitated product was collected on a filter to give 0.2 g of product as an off-white powder, m.p. 181°–183° C.

EXAMPLE 5

1,4-Bis-(4-nitrophenoxy)-2-butene

A mixture of 5.6 g of p-nitrophenol, 4.3 g of 1,4-dibromo-2-butene, and 5,6 g of $K_2CO_3$ in 80 ml of acetone was heated at 60° C. overnight. The reaction mixture was poured into water and filtered to give, after drying, 6.8 g of product as a creamy colored solid.

EXAMPLE 6

1,4-Bis-(4-aminophenoxy)butane

The Example 5 product (6 g) and 1 g of 5% Pd/C in 150 ml of EtOH was hydrogenated at 30 psi overnight and the reaction mixture then filtered. The solid compound and catalyst were boiled with EtOH, filtered, and the ethanolic solution was evaporated to give 1.5 g of a white solid.

EXAMPLE 7

1,4-Bis-[4-(N-(2-imidazolino)amino)phenoxy)butane-hydrogen iodide salt

A solution of 2 g of the Example 6 product and 4.48 g of 2-methylthioimidazoline. HI in 20 ml of pyridine was heated to relux for 2 hours. After standing at room temperature overnight, pyridine was removed under vacuo. The residue was washed successively with ether and $CH_2Cl_2$ until a creamy solid powder was obtained. Filtration gave 4.3 g of product; m.p. 130° C. (dec.).

EXAMPLE 8

Trans-2,5-Bis (4-(N-(2-imidazolino) phenyl)tetrahydrofuran

A. Trans-2,5-Bis(4-nitrophenyl)tetrahydrofuran (1)

To a mixture of Trans-2,5-Bis-phenyltetrahydrofuran (8.96 g, 0.004 mol) in 15 ml of acetic acid and 20 ml of concentrated $H_2SO_4$ is added dropwise a solution of 17.2 g (0.008 mol) of a concentrated $HNO_3$ (70%) in 20 ml of acetic acid over a period of 1 h. The reaction mixture is stirred for 1 h at room temperature and then poured into ice. The product is extracted into ethyl acetate. The organic solution is dried and evaporated to dryness. The amide product is then purified by dry column chromatography to give the desired product.

B. Trans-2,5-Bis(4-aminophenyl)tetrahydrofuran (2)

A mixture of 8 g of Compound 1 and 1 g of 5% Pd/C in 100 ml of EtOH is hydrogenated at 20 psi for 2 hours. The desired product is obtained after removal of solvent.

C. Trans-2,5-Bis(4-N-(2-imidazolino)amino)phenyl) tetrahydrofuran

A mixture of 5.18 g of Compound 2 and 5.2 g of 2-methylthio-2-imidazoline. HI in 50 ml of pyridine is heated at 110° C. for 7 hours. Solvent is removed under vacuo and the residue is washed with ether. The product is recrystallized from acetonitrile to give the desired product.

EXAMPLE 9

1,6-Bis(4-(N-(2-(3,4,5,6-tetrahydropyrimidine) amino) phenyl)hexane

A. 1,6-Bis(4-(2,5-methylthioamindino)phenyl)hexane (3).

A solution of 8.3 g (0.02 mol) of 1,6-Bis(4-thiourea)-phenyl)hexane and 4.14 g (0.003 mol; 1.5 eq) of $CH_3I$ in 50 ml of $CH_3OH$ is refluxed for 2.5 hr. Excess solvent is removed in vacuo and the residue is treated with 100 ml of saturated $Na_2CO_3$ solution. The aqueous solution is extracted with ether. The organic layer is separated, dried, concentrated and recrystallized to give the desired product (3).

B. 1.6-Bis(4-(N-(2-(3,4,5,6-tetrahydropyrimidino) amino)phenyl)hexane (4).

To 6.6 g of the above methylthioamidine (3) in 40 ml of ethylene glycol monoethyl ether is added 2.2 g (2 eq) of propylenediamine. The reaction mixture is heated at 100°–135° C. for 5 hours. The reaction mixture is concentrated and the oily residue is heated briefly with 10 ml of 6N HCl. The aqueous solution is concentrated and the residue is purified by recrystallization as a HCl salt.

EXAMPLE 10

4-Benzyloxy-N-(2-imidazolino)aniline

A solution of 2.35 g (0.01 mol) of aniline and 2.44 g (0.01 mol) of 2-Methylthioimidazoline. HI in 50 ml of pyridine was heated to reflux for 4 h. After evaporation of pyridine, the residue was treated with ether and ether was then decanted. The residue was dissolved in $CH_2Cl_2$. The organic solution was washed with $H_2O$, N-NaOH solution, $H_2O$, dried, and evaporated to give 1.5 g of produce. Recrystallization from $CH_2Cl_2$/hexane gave a crystal; mp 135°–136° C.

In a similar fashion according to the procedures of the preceding examples, the following compounds can be prepared from appropriate starting materials:

1,4-Bis-(4-(N-(2-imidazolino)amino)phenyl)-2,3-dimethylbutane;
1,6-Bis-(3-methyl-4-(N-(2-imidazolino)amino)phenyl)-hexane;
1,6-Bis(3-chloro-4-(N-(2-imidazolino)amino)phenyl)-hexane;
1,5-Bis(4-(N-(2-imidazolino)amino)phenyl)pentane;
1,5-Bis(4-(N-(2-imidazolino)amino)phenyl)-3-benzylpentane;
1,6-Bis(2-(N-(2-imidazolino)amino)phenyl)hexane.
1,4-Bis-[4-(N-(2-imidazolino)amino)phenoxy]-butane.
1,4-Bis-(4-(N-(2-imidazolino)amino)phenyl)-2,3-dimethylbutane.
1,6-Bis-(3-methyl-4-(N-(2-imidazolino)amino)phenyl)-hexane.
1,6-Bis(3-chloro-4-(N-(2-imidazolino)amino)phenyl)-hexane.
1,5-Bis(4-(N-(2-imidazolino)amino)phenyl)pentane.
1,5-bis(4-(N-(2-imidazolino)amino)phenyl)3-benzylpentane.
1,6-Bis[N-(2-(1-acetyl)imidazolino)-4-aminophenyl]hexane.
3-Methoxy-1,5-Bis(4-(N-(2-imidazolino)amino)phenyl)-pentane.
3-Ethoxy-1,5-Bis(4-(N-(2-imidazolino)amino)phenyl)-pentane.
2-Methoxy-1,6-Bis(4-(N-(2-imidazolino)amino)phenyl)-hexane.
3-Methoxy-1,6-Bis(4-(N-(2-imidazolino)amino)phenyl)-hexane.
1,3-Bis(4-(N-(2-imidazolino)amino)benzyloxy)propane.
2-Methoxy-1,3-Bis(4-(N-(2-imidazolino)amino)benzyloxy) propane.
1,6-Bis(4-(N-(2-(3,4,5,6-tetrahydropyrimidino)amino)-phenyl) hexane.

1,6-Bis(4-((N'-cyano-N"methyl)guanidino)phenyl)hexane.
1,6-Bis(4-((N'-methyl-N"-methyl)guanidino)phenyl)hexane.
4-Benzyloxy-N-(2-imidazolino)aniline.
2-Methoxy-1,3-Bis(4-N-(2-imidazolino)amino)phenyl)propane.
1-(4-(N-(2-imidazolino)amino)phenyl)-2-methoxy-3-(3,4,5-trimethoxyphenyl)propane.
1-(3,4-Dimethoxyphenyl)-3-(4-N-(2-imidazolino)amino)phenyl) propane.
1-(3,4-Dimethoxyphenyl)-3-(4-(N-(2-imidazolino)amino)phenyl)-1-methoxypropane.
4-(Imidazolino-2-amino)benzyl 3,4,5-trimethoxy)benzyl ether.
4-(imidazolino-2-amino)phenyl-3-methoxy-5-(3,4,5-trimethoxyphenyl)pentane.
Trans-2,5-Bis-(4-(N-(2-imidazolino)amino)phenyl-tetrahydrofuran.
Trans-2-(4-(N-(2-imidazolino)amino)phenyl)5-(3,4,5-trimethoxyphenyl)tetrahydrofuran.
Bis(4-(imidazolino-2-amino)benzyl)ether.
1-(4-(N-(2-imidazolino)amino)phenyl)-3-methoxy-5-phenylpentane.
1-(4-(N-(2-imidazolino)amino)phenyl)-2-methoxy-5-phenylpentane.
1-(4-(N-(2-imidazolino)amino)phenyl)1-methoxy-5-phenylpentane.
2-(4-(N-(2-imidazolino)amino)phenyl)-5-phenyl tetrahydrofuran.
Benzyl 4-(imidazolino-2-amino)benzyl ether.
N-(2-imidazolino)-4-(3-3,4,5-trimethoxyphenyl)propyl)aniline.
1-(4-N-(2-imidazolino)amino)phenyl)-1-methoxy-3-(3,4,5-trimethoxyphenyl)propane.
1-(4-N-(2-imidazolino)amino)phenyl)-2-methoxy-3-phenylpropane.
1-(3,4-Dimethoxyphenyl)-2-methoxy-3-(4-N-(2-imidazolino)amino) phenyl)propane.
Bis(4-(imidazolino-2-amino)benzyl ether.
2-(4-N-(2-(3,4,5,6-tetrahydropyrimidino)amino)phenyl)-5-(3,4,5-trimethoxy phenyl)tetrahydrofuran.
3-Methoxy-1,5-Bis(4-N-(2-(3,4,5,6-tetrahydropyrimidino)amino) phenyl)pentane.
3-Methoxy-1-(4-(N-2-imidazolino)amino)phenyl)heptane.
1-cyclohexyl-3-methoxy-5-(4-(N-(2-imidazolino)amino)phenyl)pentane.
4-(imidazolino-2-amino)benzyl benzyl ether.
Trans-2-(4-(N-(2-imidazolino)amino)phenyl)-5-phenyl-tetrahydrofuran.

The compounds of the present invention have potent activity in regulating the formation of lipoxygenease and as such possess therapeutic value in the treatment of inflammatory conditions and allergic responses such as anaphlaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicosatetraenoic acids (HETEs). Lipoxygenases are classified according to the position in the arachidonic acid which is oxygenated. Platelets metabolize arachidonic acid to 12-HETE, while polymorphonuclear leukocytes contain 5 and 15 lipoxygenases. It is known that 12HETE and 5, 12-diHETE are chemotactic for human neutrophils and eosinophils, and may augment the inflammation process. 5-HPETE is known to be a precursor of slow-reacting substance of anaphylaxis (SRS-A). The SRS family of molecules, such as leukotrienes B, C, and D, have been shown to be potent bronchoconstrictors (see, NATURE 288, 484–486 (1980)).

The following protocol describes an assay to detect inhibitors of the lipoxygenase pathway. Such inhibitors are believed to be capable of modulating the biosynthesis of the leukotrienes, a property believed to be useful in treating asthma and inflammatory disease states.

Protocol for Detecting Inhibitors of the Lipoxygenase Pathway

A suspension of rat neutrophils in buffer is incubated for 3 minutes at 30° C. with [$^{14}$C]-arachidonic acid (AA) and Calcium Ionophore A23187. Citric acid (2M) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spotted on silica gel TLC sheets, which are developed with an ethyl acetate/isooctane/water acetic acid solvent system. The 5-HETE spots are visualized with iodine, cut out and placed in scintillation vials for counting. After adjusting for the extraction efficiency, the amount (pmole) of [$^{14}$C]-5-HETE in each of the tubes is quantitated. The net of 5-HETE are obtained by subtracting the pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced.

1,6-Bis-[N-(2-imidazolino)-4-aminophenyl]hexane on such testing indicated a value, $I_{50}=1.7$ μM, illustrating potent inhibiting activity of the present new compounds.

Some compounds in this invention also display potent activities in regulating phospholipases and as such possess therapeutic value in the treatment of inflammatory conditions.

Inflammatory responses to a variety of offending stimuli are promoted by products of arachidonic acid metabolism. These products include leukotrienes (SRS-A), prostaglandins, prostacyclin and its metabolites, and thromboxanes. No matter what combination of products results from passage of substrate down the branches of this complex cascade, the initial step involves the release of arachidonic acid from phospholipids or form triglycerides containing this long-chain fatty-acid [1]. The enzymes catalayzing such release of arachidonic acid are:

[1] Borgeat, P., M. Hamberg, and B. Samuelson. Transformation of arachidonic acid and homo-linolenic acid by rabbit polymorphonuclear leukocytes. J. Biol. Chem., 251: 7816–7810 (1976).

(a) phospholipase C followed by diglyceride lipase[2];

[2] Bell, R. L., D. A. Kennerly, N. Stanford, and P.W. Majerus. Diglyceridelipase: A pathway for arachidonate release from human platelets. Proc. Nat. Acad. Sci., U.S. 76: 3238–3241 (1979).

(b) phospholipase A$_2$, either soluble or membrane-bound[3,4]; and

[3] Vadas, P., and J. B. Hay. The release of phospholipase A$_2$ from aggregated platelets and stimulated macrophages of sheep. Life Sciences, 26: 1721–1729 (1980).

[4] Franson, R. C., D. Eisen, R. Jesse and C. Lanni. Inhibition of highly purified mammalian phospholipases A$_2$ by non-steroidal anti-inflammatory agents, modulation by calcium ions. Biochemical J. 186: 633–636 (1980).

(c) a lipase able to degrade triglycerides that contain arachidonic acid[1].

[1] Borgeat, P., M. Hamberg, and B. Samuelson. Transformation of arachidonic acid and homo-linolenic acid by rabbit polymorphonuclear leukocytes. J. Biol. Chem., 251: 7816–7810 (1976).

An assay has been developed to test the ability of the invented compounds on the activity of the phospholipases. In this protocol, a procedure is described for testing the inhibitory effects of these compounds on phospholipase C (PLC).

Protocol for In Vitro Assay for Inhibitors of Phospholipase

The PLC employed in this screen is obtained by aggregation of purified rat platelets in the presence of $CaCl_2$ and ADP. In the enzyme assay, phosphatidylinositol having $^3H$-labeled arachidonate residues at R2 is employed as substrate. PLC acts by cleaving the phosphate ester bond yielding diglyceride as follows:

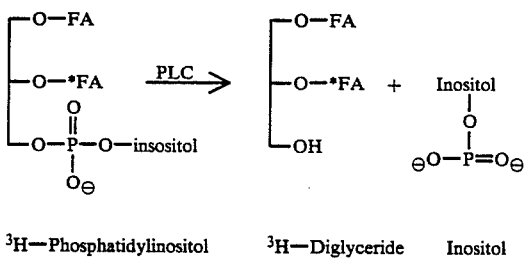

Following completion of the reaction, the assay medium is acidified and extracted with hexane which takes up unreacted substrate and diglyceride. The hexane extract is passed over a short silica gel column which retains 99% of the phosphatidylinositol. The $^3H$-labeled diglyceride is not retained (95% recovery in eluate) and is collected directly in scintillation counting vials. The diglyceride is conveniently quantitated by liquid scintillation spectrometry.

The compounds were tested at 300 μM in a buffer containing 0.06 mM unlabeled phosphatidylcholine (PC), 20–30,000 cpm of $^{14}C$ [PC], 150 mM NaCl, 5 mM $CaCl_2$ and 50 mM Tris(hydroxymethyl) methylaminopropanesulfonic acid buffer, adjusted to pH 9.0 with 1N NaOH. The temperature of the buffer is maintained at a temperature of 37° C. The reaction was initiated by addition of the enzyme and it was terminated 10 minutes later by addition of 1 ml of 1N HCL.

Following acidification, the samples were extracted with 2 ml of isopropyl alcohol and 2 ml of hexane, vortexed and allowed to stand until the phases separate. Free inositol and some unreacted substrate were taken up in the isopropanol-saturated hexane. The hexane phase of the extraction mixture was transferred to a short silica gel column which retained unreacted phosphatidylinositol, but not the $^3H$-diglyceride. The column effluent was collected directly in scintillation vials. The columns were washed once with additional 2 ml of hexane. The radiolabeled diglycerides were quantitated by liquid scintillation spectrometry.

1,6-Bis-[N-(2-imidazolino)-4-aminophenyl]-hexane on such testing indicated a value of $I_{50}=14$ μM illustrating potent acitivity of the present new compounds.

PAF BINDING PROTOCOL

I. INTRODUCTION

Platelet activating factor (PAF) has been shown to be a potent mediator involved in IgE anaphylaxis, suggesting an involvement in inflammation and asthma. PAF has been shown to aggregate platelets and polymorphonuclear leukocytes and to cause secretion of their contents (Benveniste et al., 1979; Goetzel et al., 1980; Henson 1970; O'Flaherty et al., 1980; Shaw et al., 1981). Some of the other effects reported for PAF include smooth muscle contraction (Findlay et al., 1981); hypotension (Blank et al., 1979; Muirhead et al., 1981); leukocyte chemotaxis (O'Flaherty et al., 1980; Shaw et al., 1981); activation of lipoxygenase in human polymorphonuclear leukocytes and isolated lung (Lin et al., 1982; Voelkel et al., 1982). The structure of PAF has been recently identified as 1-O-alkyl-2-O-acetyl-sn-glycero-3-phosphorylcholine with the alkyl group being either a hexadecyl or octadecyl chain (Benveniste et al., 1979; Demopoulas et al., 1979).

The binding of PAF has been described with both intact platelets and membranes isolated from platelets (Shaw and Henson, 1980; Brown and Thuy, 1981; Mowles et al., 1982; Valone et al., 1982, Hwang et al., 1983; Shen et al., 1985). This protocol describes a modification of these reported methods to identify specific binding sites for radiolabeled PAF on membranes from rabbit platelets.

LITERATURE CITED

Beneveniste, J., Tence, M., Bidault, J., Boullet, C. and Polonsky, J. 1979. Semisynthese et structure proposee du facteur activant les plaquettes (PAF): PAF-Acether, un alkyl ether analogue de la lysophosphatidylcholine. Compt. Rend. Acad. Sci. Paris, 289D:1037–1040.

Blank, M. L., Snyder, F., Byer, L. W., Brooks, B. and Muirhead, E. E. 1979. Antihypertensive activity of an alkyl ether analog of phosphatidylcholine. Biochem. Biophys. Res. Commun. 90:1194–1200, 1979.

Brown, J. E. and Thug, L. P. 1981. The binding of bovine platelet aggregating factor to human platelets. Thromb. Res. 22:41–51.

Demopoulos, C. A., Pinckard, R. N. and Hanahan, D. J. 1979. Platelet-activating factor. Evidence for 1-O-alkyl-2-acetyl-sn-gylceryl-3-phosphoryl-choline as the active component (a new class of lipid chemical mediators). J. Biol. Chem. 254:9355–9358.

Findley, S. R., Lichtenstein, L. M., Hanahan, D. J. and Pinckard, R. N. 1981. Contraction of guinea pig ileal smooth muscle by acetyl glyceryl ether phosphorylcholine. Am. J. Physiol. 241: (Cell Physiol. 10), C130–C133.

Goetzel, E. J. Derrian, C. K. Tauber, A. I. and Valone, F. H. 1980. Novel effects of 1-O-hexadecyl-2-O-acyl-sn-glycero-3-phosphorylcholine mediators on human leukocyte function: delineation of the specific roles of the acyl substitutes. Biochem. Biophys. Res. Comm. 94:881–888.

Henson, P. M. 1970. Release of vasoactive amines from rabbit platelets induced by sensitized mononuclear leukocytes and antigen. J. Exp. Med. 131:287–304.

Hoffman, B., Michel, T. Brenneman, T. and Lefkowitz, R. 1982. Interactions of agonists with platelet alpha$_2$-adrenergic receptors. Endocrinology 110:926–932.

Hwang, S., Lee, C. C., Cheah, M. J. and Shen, T. Y. 1983. Specific receptor sites for 1-O-alkyl-2-O-acetyl-sn-glycero-3-phosphocholine (Platelet Activating Factor) on rabbit platelet and guinea pig smooth muscle membranes. Biochemistry 22:4756–4763.

Lin, A. H., Morton, D. R. and Gorman, R. R. 1982. Acetyl glyceryl ether phosphorylcholine stimulate leukotriene B4 synthesis in human polymorphonuclear leukocytes. J. Clin. Invest. 70:1058–1065.

Lowry, O., Rosenbrough, L., Farr, L. and Randall, R. 1949. Protein Measurement with Folin phenol reagent. J. Biol. Chem. 193:265–275.

Mowles, T. F., Burghardt, B., Tsien, W. H. and Shepard, H. 1982. Radioreceptor binding assay for platelet activating factor. Fed. Proc. (Abstract) 41:1459.

Muirhead, E. E., Byer, L. W., Desiderio, D., Jr., Smith, K. A., Prewitt, R. L. and Brooks, B. 1981. Alkyl ether analogs of phosphatidylcholine are orally active in hypertensive rabbits. Hypertension 3 (Supp. 1):107–111.

O'Flaherty, J. R., Wykle, R. L., Miller, C. H., Lewis, J. C., White, M., Bass, D. A., McCall, C. E. and DeChatelet, L. R. 1980. 1-O-alkyl-2-O-acetyl-sn-glyceryl-3-phosphocholines: A novel class of neutrophil stimulants. Am. J. Pathol. 103:70–78.

O'Flaherty, J. T., Wykle, R. L. Lees, C. J., Shewmake, T., McCall, C. E. and Thomas, M. J. 1980. Neutrophil-degranulating action of 5, 12-dihydroxy-6,8,10,14-eicosatetraenoic acid and 1-O-alkyl-2-O-acetyl-sn-clycero-3-phosphocholine: Comparison with other degranulating agents. Am. J. Pathol. 105, 264–269.

Scatchard, G. 1949. The attractions of proteins for small molecules and ions. Ann. N.Y. Acad. Sci. 51:660–672.

Shaw, J. O. and Henson, P. M. 1980. The binding of rabbit basophil-derived platelet-activating factor to rabbit platelets. Am. J. Pathol. 98, 791–810.

Shaw, J. O., and Pinckard, R. N., Ferrigni, K. S., McManus, L. M. and Hannahan, D. J. 1981. Activation of human neutrophils with 1-O-hexadecyl/octadecyl-2-acetyl-sn-glyceryl-3-phosphorylcholine (platelet activating factor). J. Immunol. 127, 1250–1255.

Shen, T. Y., Hwang, S., Chang, M. N., Doebber, T. W., Lam, M. T., Wu, M. S., Wang, X., Han, G. Q. and Li. R. Z. 1985. Characterization of a platelet-activating factor receptor antagonism isolated from haifenteng (Piper Futokadsura): specific inhibition of in vitro and in vivo platelet-activating factor-induced effects. Proc. Natl. Acad. Sci. 82:672–676.

Valone, F. H., Coles, E., Reinhold, V. R. and Goetzl, E. J. 1982. Specific binding phospholipid platelet-activating factor by human platelets. J. Immunol. 1294:1637–1641.

Voelkel, N. F., Worthen, Reeves, J. T., Hensen, P. M. and Murphy, R. C. 1982. Nonimmunological production of leukotrienes induced by platelet activating factor, Science 218:286–288.

II. METHODS

A. Preparation of the crude receptor fraction:

This procedure was adapted from Hoffman et al. (1982) and Hwang et al. (1983). Male rabbits were anesthetized with 30 mg/kg nembutal ® and then blood was collected from the abdominal aorta into tubes containing 1.0 ml of 100 mM EDTA (pH 7.0) per each 50 ml blood. The blood was transferred to 50 ml centrifuge tubes and the Platelet Rich Plasma (PRP) was obtained by centrifugations at 380×g for 10 min at 25°. The PRP was carefully removed and re-centrifuged at 16,000×g for 10 min at 4°. The platelet pellet was resuspended and washed 3 times with platelet wash buffer (150 mM NaCl, 50 TRIS-Cl, 20 mM EDTA, pH 7.5) and homogenized with 30 strokes with a teflon-tipped pestle in Duall ® homogenizer maintained at 4°. The platelet membrane were obtained by centrifugation at 30,000×g for 10 min. The resulting pellet was resuspended in the hypotonic buffer and centrifuged at 30,000×g for 10 min. The final pellet was resuspended in assay buffer minus BSA (10 mM TRIS-Cl, 150 mM choline chloride, pH 7.5) to one-tenth the volume of the original blood sample. An aliquot is taken to determine the protein concentratin of the washed platelet preparation by the method of Lowry (1949) using BSA as the standard. Assay buffer and sufficient 3% BSA are added to obtain a final solution of 0.25% BSA and 750 ug platelet protein per 1 ml. (Protein Preparation).

B. Binding Assay:

Each assay tube (16×100 mm) contains the following:

(a) 790 ul Assay BUffer (10 mM Tris-Cl (pH 7.5 at RT), 150 mM chlorine chloride 0.25% BSA.

(b) 10 ul Test compound or solvent-If possible, dissolve compounds in Assay buffer to a concentration 100-fold higher than the highest desired concentration for testing. Serially dilute the compound in Assay Buffer so that all dilutions are 100-fold higher than the assay concentration desired. If compounds are insoluble in buffer, dissolve them in either DMSO or ethanol. Preferably, final assay concentrations of DMSO and ethanol should be kept under 0.1% and 1% (v/v), respectively. However, assay concentrations as high as 1% DMSO and 2% ethanol have no measurable effects on binding and can be used if necessary.

(c) 100 ul $^3$H-PAF (ca. 17,500 DPM)-[$^3$H-PAF is alkyl-2-acetyl-sn-glyceryl-3-phosphocholine 1-0[alkyl-1', 2', $^3$H, 30–60 Ci/mmol]

(d) 100 ul Protein preparation

Incubations are done at 25° for 30 min in a shaking water bath. Reactions are started by the addition of the protein preparation. At the end of the incubation time, 4.0 ml of cold wash buffer is added to the tube. After being vortexed, the contents of the tube are immediately poured over a Whatman GF/C Filter (25 mm diameter) which is sitting in a vacuum manifold (e.g. Millipore Model No. 3025 manifold) to which a partial vacuum is applied. The filters are immediately washed with an additional 15 ml of cold buffer. The filters are transferred to 7 ml plastic scintillation vials to which 6.0 ml of appropriate scintillation fluid (e.g., Scintiverse ®) is added. After being allowed to equilibrate for 4–6 hours, the radioactivity is counted with a liquid scintillation counter appropriately set for tritium.

1,6-Bis-[N-(2-imidazolino-4-aminophenyl)hexane on testing as a PAF antagonist exhibited a value of $I_{50} = 1.2$ µM, illustrating the potent activity of the present new compounds.

The above embodiments and examples are given to illustrate the scope and spirit of the present invention. These embodiments and examples will make apparent to those skilled in the art, other embodiments and examples. Thses other embodiments and examples are within the contemplation of the present invention.

In the formulas of the present invention, one skilled in the art will understand that all of the atoms have the correct valences. The various tautomeric forms are contemplated to be within the scope of the present invention. Unless designated otherwise, it is understood that the various atoms are substituted by hydrogen in order to maintain the appropriate valences. For example

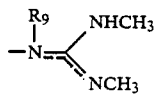

is equivalent to the two following structures:

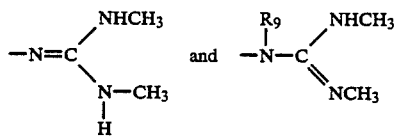

What is claimed is:

1. A compound of the formula:

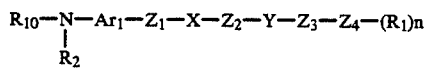

or a pharmaceutically acceptable salt thereof; wherein
Ar$_1$ is phenyl or naphthyl;
X and Y are independently O, S or a chemical bond;
Z$_1$ and Z$_3$ are each a chemical bond or alkylene chain having up to 8 carbon atoms in the principal chain and up to a total of 12 carbon atoms;
Z$_2$ and Z$_4$ are each a chemical bond, alkylene chain having up to 6 carbon atoms in the principal chain and a total of up to 10 carbon atoms, carbocyclic aryl, cycloalkyl, or tetrahydrofuran;
each of Z$_1$, Z$_2$, Z$_3$ and Z$_4$ is substituted or unsubstituted;
each R$_1$ is independently hydrogen, lower alkyl, carbocyclic aryl, lower carbocyclic aralkyl, hydroxy, lower alkoxy, carboxy, lower carbocyclic carbaralkoxy, lower carbocyclic carbaryloxy, lower alkoxy carbonyl, lower alkanoyl, cyano, halogen, amino, lower alkenyl, lower alkynyl, lower cycloalkyl,

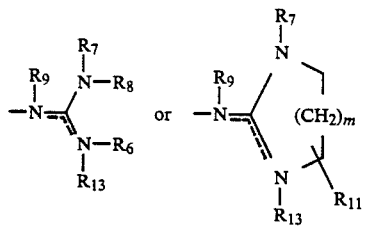

R$_2$, R$_5$, R$_7$, R$_9$ and R$_{13}$ are independently hydrogen, lower alkyl or lower alkanoyl; but when the nitrogen to which R$_2$ is attached contains a double bond, then R$_2$ is a bond and becomes part of the double bond, when the nitrogen to which R$_9$ is attached contains a double bond, then R$_9$ is a bond and becomes part of the double bond, or when the nitrogen to which R$_{13}$ is attached contains a double bond, then R$_{13}$ is a bond and becomes part of the double bond;
R$_3$, R$_4$, R$_6$ and R$_8$ are independently hydrogen, lower alkyl, cyano, or nitro;
R$_{10}$ is

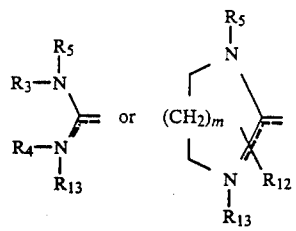

R$_{11}$ and R$_{12}$ are independently hydrogen, or lower alkyl;
n is 0, 1, 2, or 3 and
m is 0;
provided that (1) when Z$_2$ is a chemical bond or methylene group, X and Y cannot be both oxygen or sulfur and (2) at least one of R$_1$ and R$_{10}$ contains an imidazolino group.

2. The compound according to claim 1 wherein Ar$_1$ is phenyl.

3. The compound according to claim 1 wherein Z$_4$ is phenyl or tetrahydrofuran.

4. The compound according to claim 1 wherein R$_2$ is hydrogen.

5. The compound according to claim 1 wherein R$_{10}$ is

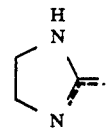

6. The compound according to claim 1 wherein X and Y are each independently O or a chemical bond.

7. The compound according to claim 1 wherein Z$_1$, Z$_2$ and Z$_3$ are independently a chemical bond or alkylene chain containing up to 3 carbon atoms in the principal chain.

8. The compound according to claim 1 wherein R$_1$ is H, lower alkoxy, or

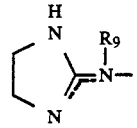

wherein R$_9$ is independently hydrogen lower alkyl or lower alkanoyl but when the nitrogen to which R$_9$ is attached contains a double bone, then R$_9$ is a bond and becomes part of the double bond.

9. The compound according to claim 1 wherein when Z$_1$, Z$_2$, and Z$_3$ are other than a chemical bond, Z$_1$, Z$_2$ and Z$_3$ are each monosubstituted with hydrogen, lower alkyl, aryl, lower aralkyl, hydroxy, lower alkoxy, lower aralkoxy or aryloxy, wherein aryl, alone or as part of a group, is carbocyclic aryl.

10. The compound according to claim 1 wherein the lower alkoxy group is methoxy or ethoxy.

11. A compound of the formula:

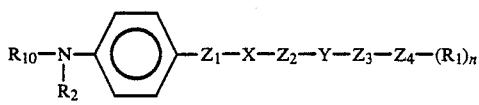

and or a pharmaceutically acceptable salt thereof wherein
X and Y are independenly O, S or a chemical bond;
$Z_1$ and $Z_3$ are each a chemical bond or alkylene chain having up to 8 carbon atoms in the principal chain and up to a total of 12 carbon atoms;
$Z_2$ and $Z_4$ are each chemical bond, alkylene chain having up to 6 carbon atoms in the principal chain and total of up to 10 carbon atoms, carbocyclic aryl, cycloalkyl, or tetrahydrofuran;
each of $Z_1$, $Z_2$, $Z_3$ and $Z_4$ is substituted or unsubstituted;
each $R_1$ is independently hydrogen, lower alkyl, carbocyclic aryl, lower carbocyclic aralkyl, hydroxy, lower alkoxy, carboxy, lower carbocyclic carbaralkoxy, lower carbocyclic carbaryloxy, lower alkoxy carbonyl, lower alkanoyl, cyano, halogen, amino, lower alkenyl, lower alkynyl, lower cycloalkyl,

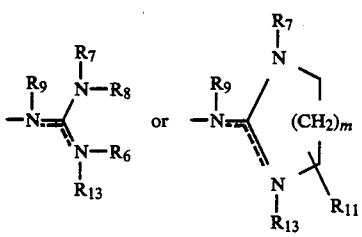

$R_2$, $R_5$, $R_7$, $R_9$ and $R_{13}$ are independently hydrogen, lower alkyl or lower alkanoyl; but when the nitrogen to which $R_2$ is attached contains a double bond, then $R_2$ is a bond and becomes part of the double bond, when the nitrogen to which $R_9$ is attached contains a double bond, then $R_9$ is a bond and becomes part of the double bond, or when the nitrogen to which $R_{13}$ is attached contains a double bond, then $R_{13}$ is a bond and becomes part of the double bond;
$R_3$, $R_4$, $R_6$ and $R_8$ are independently hydrogen, lower alkyl, cyano, or nitro;
$R_{10}$ is

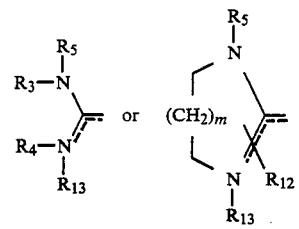

$R_{11}$ and $R_{12}$ are independently hydrogen, or lower alkyl;
n is 0, 1, 2, or 3 and
m is 0;
provided that (1) when $Z_2$ is a chemical bond or methylene group, X and Y cannot be both oxygen or sulfur and (2) at least one of $R_1$ and $R_{10}$ contains an imidazolino group.

12. The compound according to claim 11 wherein $Z_4$ is phenyl.

13. The compound according to claim 11 wherein $R_2$ is hydrogen.

14. The compound according to claim 11 wherein $R_{10}$ is

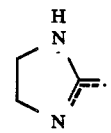

15. The compound according to claim 11 wherein X and Y are each independently 0 or a chemical bond:

16. The compound according to claim 11 wherein $Z_1$, $Z_2$ and $Z_3$ are independently a chemical bond or alkylene chain containing up to 3 carbon atoms in the principal chain.

17. The compound according to claim 11 wherein $R_1$ is H, or lower alkoxy, or

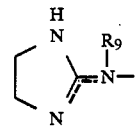

wherein $R_9$ is independently hydrogen lower alkyl or lower alkanoyl but when the nitrogen to which $R_9$ is attached contains a double bond, then $R_9$ is a bond and becomes part of the double bond.

18. The compound according to claim 11 wherein when $Z_1$, $Z_2$, and $Z_3$ are other than a chemical bond, $Z_1$, $Z_2$ and $Z_3$ are each monosubstituted with hydrogen, lower alkyl, aryl, lower aralkyl, hydroxy, lower alkoxy, lower aralkoxy or aryloxy, wherein aryl, alone or as part of a group, is carbocyclic aryl.

19. The compound according to claim 11 wherein the lower alkoxy group is methoxy or ethoxy.

20. A compound of the formula:

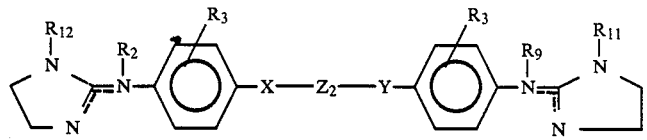

or a pharmaceutically acceptable salt thereof; wherein:
Z₂ is an alkylene chain of up to 8 carbon atoms in the principal chain and up to a total of about 12 carbon atoms which may be mono- or disubstituted with hydrogen, lower alkyl, phenyl, benzyl or lower alkoxy;

X and Y are independently oxygen, sulfur or a chemical bond;

R₃ is hydrogen, lower alkyl or halogen;

R₂, R₉, R₁₁ and R₁₂ are independently hydrogen, lower alkyl or lower alkanoyl, but when the nitrogen to which R₂ is attached contains a double bond, then R₂ is a bond and becomes part of the double bond, or when the nitrogen to which R₉ is attached contains a double bond, then R₉ is a bond and becomes part of the double bond.

21. The compund according to claim 20 wherein each R₂, R₉, R₁₁, and R₁₂ are hydrogen, and X and Y are oxygen.

22. A compound according to claim 20 wherein X and Y are chemical bonds.

23. The compound according to claim 20 wherein Z₂ is an alkylene chain containing from 4 to 6 carbon atoms in the principal chain.

24. A compound of the structure

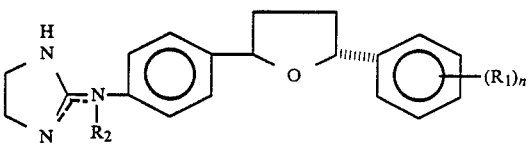

or a pharmaceutically acceptable salt thereof wherein R₁ is H, lower alkoxy, or

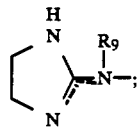

n is 0,1,2 or 3;

R₂ is hydrogen, but when the nitrogen to which R₂ is attached forms a double bond with the carbon on the imidazoline ring, then R₂ is a bond and becomes part of a double bond;

and R₉ is independently hydrogen, lower alkyl or lower alkanoyl but when the nitrogen to which R₉ is attached contains a double bond, then R₉ is a

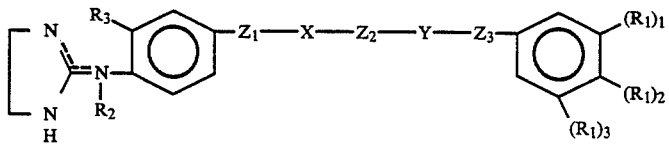

or a pharmaceutically acceptable salt thereof, wherein
X is chemical bond or O,
Y is chemical bond or O,
Z₁ and Z₃ are independently chemical bonds or an unsubstituted normal alkylene chain of up to 5 carbons;
Z₂ is a chemical bond,

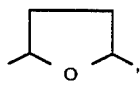

or an unsubstituted normal alkylene chain of up to 5 carbon atoms, or a substituted alkylene chain having up to 5 carbon atoms, wherein the substitution is methoxy or ethoxy:
(R₁)₁, is H, methoxy, CH₃ or Cl
(R₁)₂ is H, methoxy or

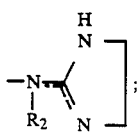

(R₁)₃ is H or methoxy;
R₃ is H, CH₃ or Cl; and
R₂ is H or acetyl, but when the nitrogen to which R₂ is attached contains a double bond, then R₂ is a bond and becomes part of the double bond.

25. A compound of the formula:

bond and becomes part of the double bond.

26. The compound according to claim 20 which is 3-Methoxy-1,5-Bis(4-(N-(2-imidazolino)amino)phenyl)-pentane.

27. The compound according to claim 20 which is 3-Ethoxy-1,5-Bis(4-(N-(2-imidazolino)amino)phenyl)-pentane.

28. The compound according to claim 20 which is 2-Methoxy-1,6-Bis(4-(N-(2-imidazolino)amino)phenyl)-hexane.

29. The compound according to claim 20 which is 3-Methoxy-1,6-Bis(4-(N-(2-imidazolino)amino)phenyl)-hexane.

30. The compound according to claim 20 which is 1,3-Bis(4-(N-(2-imidazolino)amino)benzyloxy)propane.

31. The compound according to claim 20 which is 2-Methoxy-1,3-Bis(4-(N-(2-imidazolino)amino)benzyloxy) propane.

32. The compound according to claim 24 which is 4-Benzyloxy-N-(2-imidazolino)aniline.

33. The compound according to claim 20 which is 2-Methoxy-1,3-Bis(4-(N-(2-imidazolino)amino)phenyl)-propane.

34. The compound according to claim 24 which is 1-(4-(N-(2-imidazolino)amino)phenyl)-2-methoxy-3-(3,4,5-trimethoxyphenyl)propane.

35. The compound according to claim 24 which is 1-(3,4-Dimethoxyphenyl)-3-(4-(N-(2-imidazolino)amino)phenyl) propane.

36. The compound according to claim 24 which is 1-(3,4-Dimethoxyphenyl)-3-(4-(N-(2-imidazolino)amino)phenyl)-1-methoxypropane.

37. The compound according to claim 24, which is 4-(Imidazolino-2-amino)benzyl (3,4,5-trimethoxy)benzyl ether.

38. The compound according to claim 24 which is 4-(Imidazolino-2-amino)phenyl-3-methoxy-5-(3,4,5-trimethoxyphenyl)pentane.

39. The compound according to claim 24 which is Trans- 2,5-Bis(4-(N-(2-imidazolino)amino)phenyl)tetrahydrofuran.

40. The compound according to claim 24 which is 2-(4-(N-(2-Imidazolino)amino)phenyl)-5-(3,4,5-trimethoxyphenyl)tetrahydrofuran.

41. The compound according to claim 20 which is Bis(4-(Imidazolino-2-amino)benzyl ether.

42. The compound 3-Methoxy-1-(4-(N-(2-imidazolino)amino)phenyl)heptane.

43. The compound 1-cyclohexyl-3-methoxy-5-(4-(N-(2-imidazolino)amino)phenyl)pentane.

44. The compound 4-(Imidazolino-2-amino)benzyl benzyl ether.

45. The compound trans-2-(4-(N-(2-imidazolino)amino)phenyl)-5-phenyltetrahydrofuran.

46. A therapeutic composition for treating asthma or inflammatory or allergic conditions comprising an effective amount of a compound according to claim 1 and a pharmaceutical carrier therefor.

47. A method of treating asthma or inflammatory or allergic conditions in a mammal comprising the administration of a therapeutically effective amount of a compound according to claim 1.

* * * * *